United States Patent
Wang et al.

(10) Patent No.: US 10,824,326 B2
(45) Date of Patent: Nov. 3, 2020

(54) REMOTE INTERFACING WITH A NETWORKED DIALYSIS SYSTEM

(71) Applicant: Fresenius Medical Care Holdings, Inc., Waltham, MA (US)

(72) Inventors: Fei Wang, Concord, CA (US); Martin Crnkovich, Walnut Creek, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 0 days.

(21) Appl. No.: 16/133,808

(22) Filed: Sep. 18, 2018

(65) Prior Publication Data

US 2019/0114048 A1 Apr. 18, 2019

Related U.S. Application Data

(60) Continuation of application No. 14/190,962, filed on Feb. 28, 2014, now Pat. No. 10,734,438, which is a (Continued)

(51) Int. Cl.
*G09G 5/00* (2006.01)
*G06F 3/0488* (2013.01)
(Continued)

(52) U.S. Cl.
CPC .......... *G06F 3/0488* (2013.01); *G06F 19/00* (2013.01); *G16H 40/63* (2018.01); *G16Z 99/00* (2019.02)

(58) Field of Classification Search
CPC .......... G06F 3/04883; G06F 3/04812; G06F 3/0488; G06F 2203/04808; G06F 19/3406;
(Continued)

(56) References Cited

U.S. PATENT DOCUMENTS

| 2,887,109 A | 5/1959 | Barrington |
| 2,939,770 A | 6/1960 | Schwartzkopff |

(Continued)

FOREIGN PATENT DOCUMENTS

| DE | 10049393 A1 | 4/2002 |
| EP | 1271386 A2 | 1/2003 |

(Continued)

OTHER PUBLICATIONS

[No Author Listed] Fresenius Medical Care, "Dialysis Products" 2008. 2 pages.

(Continued)

*Primary Examiner* — Hau H Nguyen
(74) *Attorney, Agent, or Firm* — Davis Malm & D'Agostine, P.C.; David J. Powsner

(57) ABSTRACT

A networked dialysis system includes a dialysis machine, a user interface, and a device that is located remotely from the dialysis machine and that exchanges information with the dialysis machine via a networked communications link. A digital data processor, which is coupled to the dialysis machine and to the remote device, facilitates execution of services on one or more remote digital data processing systems. The digital data processor is coupled to the remote device via the networked communications link and is coupled to the dialysis machine via a second communications link.

19 Claims, 9 Drawing Sheets

Related U.S. Application Data division of application No. 12/355,082, filed on Jan. 16, 2009, now Pat. No. 8,698,741.

(51) Int. Cl.
*G16H 40/63* (2018.01)
*G16Z 99/00* (2019.01)
*G06F 19/00* (2018.01)

(58) Field of Classification Search
CPC .... G06F 3/0236; G06F 3/048; G06F 19/3418; G06F 3/0482; G06F 19/3481; G06F 19/34; G06F 9/451; A61M 1/28; A61M 2205/3553; A61M 2205/502; A61M 1/14
See application file for complete search history.

(56) References Cited

U.S. PATENT DOCUMENTS

| | | |
|---|---|---|
| 3,637,997 A | 1/1972 | Petersen |
| 4,245,244 A | 1/1981 | Lijewski et al. |
| 4,248,226 A | 2/1981 | Pitchford, Jr. |
| 4,396,383 A | 8/1983 | Hart |
| 4,614,267 A | 9/1986 | Larkin |
| 4,737,036 A | 4/1988 | Offermann |
| 4,936,446 A | 6/1990 | Lataix |
| 5,025,523 A | 6/1991 | Zappa et al. |
| 5,185,597 A | 2/1993 | Pappas et al. |
| 5,276,611 A | 1/1994 | Ghiraldi |
| 5,283,560 A | 2/1994 | Bartlett |
| 5,293,470 A | 3/1994 | Birch et al. |
| 5,304,173 A | 4/1994 | Kittrell et al. |
| 5,345,250 A | 9/1994 | Inoue et al. |
| 5,367,316 A | 11/1994 | Ikezaki |
| 5,389,947 A | 2/1995 | Wood et al. |
| 5,396,281 A | 3/1995 | Maeda |
| 5,401,238 A | 3/1995 | Pirazzoli |
| 5,431,496 A | 7/1995 | Balteau et al. |
| 5,434,626 A | 7/1995 | Hayashi et al. |
| 5,690,813 A | 11/1997 | Coale |
| 5,781,442 A | 7/1998 | Engleson et al. |
| 5,798,752 A | 8/1998 | Buxton et al. |
| 5,825,352 A | 10/1998 | Bisset et al. |
| 5,838,291 A | 11/1998 | Ohshima et al. |
| 5,850,221 A | 12/1998 | Macrae et al. |
| 5,858,239 A | 1/1999 | Kenley et al. |
| 5,865,745 A | 2/1999 | Schmitt et al. |
| 5,900,859 A | 5/1999 | Takishita et al. |
| 5,903,211 A | 5/1999 | Flego et al. |
| 5,933,136 A | 8/1999 | Brown |
| 5,946,659 A | 8/1999 | Lancelot et al. |
| 6,036,357 A | 3/2000 | Van Drie |
| 6,057,826 A | 5/2000 | Gaultier et al. |
| 6,067,157 A | 5/2000 | Altendorf |
| 6,118,430 A | 9/2000 | Igari |
| 6,143,181 A | 11/2000 | Falkvall et al. |
| 6,146,523 A | 11/2000 | Kenley et al. |
| 6,151,581 A | 11/2000 | Kraftson et al. |
| 6,228,047 B1 | 5/2001 | Dadson |
| 6,335,725 B1 | 1/2002 | Koh et al. |
| 6,335,761 B1 | 1/2002 | Glen et al. |
| 6,359,631 B2 | 3/2002 | DeLeeuw |
| 6,379,032 B1 | 4/2002 | Sorensen |
| 6,462,786 B1 | 10/2002 | Glen et al. |
| 6,469,695 B1 | 10/2002 | White |
| 6,481,571 B1 | 11/2002 | Kelders et al. |
| 6,493,002 B1 | 12/2002 | Christensen |
| 6,493,747 B2 | 12/2002 | Simmon et al. |
| 6,507,868 B2 | 1/2003 | Simmon et al. |
| 6,574,503 B2 | 6/2003 | Ferek-Petric |
| 6,684,379 B2 | 1/2004 | Skoll et al. |
| 6,736,789 B1 | 5/2004 | Spickermann |
| 6,738,052 B1 | 5/2004 | Manke et al. |
| 6,746,398 B2 | 6/2004 | Hervy et al. |
| 6,820,050 B2 | 11/2004 | Simmon et al. |
| 6,912,664 B2 | 6/2005 | Ranganathan et al. |
| 6,919,269 B2 | 7/2005 | Schneegans et al. |
| 6,982,727 B2 | 1/2006 | Baer et al. |
| 7,015,899 B2 | 3/2006 | Kim |
| 7,038,588 B2 | 5/2006 | Boone et al. |
| 7,044,927 B2 | 5/2006 | Mueller et al. |
| 7,088,343 B2 | 8/2006 | Smith et al. |
| 7,134,966 B1 | 11/2006 | Tice |
| 7,154,397 B2 | 12/2006 | Zerhusen et al. |
| 7,170,500 B2 | 1/2007 | Canova, Jr. |
| 7,185,282 B1 | 2/2007 | Naidoo et al. |
| 7,188,151 B2 | 3/2007 | Kumar |
| 7,190,352 B2 | 3/2007 | Ling et al. |
| 7,215,991 B2 | 5/2007 | Besson et al. |
| 7,284,262 B1 | 10/2007 | Meric et al. |
| 7,336,187 B2 | 2/2008 | Hubbard, Jr. et al. |
| 7,351,340 B2 | 4/2008 | Connell et al. |
| 7,584,108 B2 | 9/2009 | Brown |
| 7,627,334 B2 | 12/2009 | Cohen et al. |
| 7,685,005 B2 | 3/2010 | Riff et al. |
| 7,722,594 B1 | 5/2010 | Frezza |
| 7,801,598 B2 | 9/2010 | Zhu et al. |
| 7,801,746 B2 | 9/2010 | Moll et al. |
| 7,866,465 B2 | 1/2011 | Dverin |
| 7,956,847 B2 | 6/2011 | Christie |
| 8,100,770 B2 | 1/2012 | Yamazaki et al. |
| 8,182,440 B2 | 5/2012 | Cruz et al. |
| 8,500,694 B2 | 8/2013 | Susi |
| 8,543,420 B2 | 9/2013 | Darby et al. |
| 8,632,485 B2 | 1/2014 | Schlaeper et al. |
| 8,698,741 B1 | 4/2014 | Wang et al. |
| 8,970,503 B2 | 3/2015 | Christie et al. |
| 8,974,414 B2 | 3/2015 | Alisantoso et al. |
| 10,078,438 B2 | 9/2018 | Wang et al. |
| 10,299,633 B2 | 5/2019 | Shaw |
| 10,646,634 B2 | 5/2020 | Yu et al. |
| 2001/0005115 A1 | 6/2001 | Busio et al. |
| 2001/0011036 A1 | 8/2001 | Miyamoto et al. |
| 2001/0016056 A1 | 8/2001 | Westphal et al. |
| 2001/0034614 A1 | 10/2001 | Fletcher-Haynes et al. |
| 2001/0045395 A1 | 11/2001 | Kitaevich et al. |
| 2001/0050610 A1 | 12/2001 | Gelston |
| 2001/0056226 A1 | 12/2001 | Zodnik et al. |
| 2002/0032385 A1 | 3/2002 | Raymond et al. |
| 2002/0035637 A1 | 3/2002 | Simmon et al. |
| 2002/0082728 A1 | 6/2002 | Mueller et al. |
| 2002/0107449 A1 | 8/2002 | Roeher |
| 2002/0118595 A1 | 8/2002 | Miller et al. |
| 2002/0163178 A1 | 11/2002 | Williams |
| 2002/0198473 A1 | 12/2002 | Kumar et al. |
| 2003/0001743 A1 | 1/2003 | Menard |
| 2003/0018395 A1 | 1/2003 | Crnkovich et al. |
| 2003/0069481 A1 | 4/2003 | Hervy et al. |
| 2003/0083901 A1 | 5/2003 | Bosch et al. |
| 2003/0135392 A1 | 7/2003 | Vrijens et al. |
| 2003/0141981 A1 | 7/2003 | Bui et al. |
| 2003/0150748 A1 | 8/2003 | Crawley |
| 2003/0158508 A1 | 8/2003 | DiGianfilippo et al. |
| 2003/0197690 A1 | 10/2003 | Zimenkov |
| 2003/0198406 A1 | 10/2003 | Bibbo et al. |
| 2003/0218935 A1 | 11/2003 | Hu |
| 2003/0220607 A1 | 11/2003 | Busby et al. |
| 2004/0021673 A1 | 2/2004 | Alessi et al. |
| 2004/0027912 A1 | 2/2004 | Bibbo et al. |
| 2004/0047232 A1 | 3/2004 | Terentiev |
| 2004/0104250 A1 | 6/2004 | Rousselet |
| 2004/0111293 A1 | 6/2004 | Firanek et al. |
| 2004/0111294 A1 | 6/2004 | McNally et al. |
| 2004/0128162 A1 | 7/2004 | Schlotterbeck et al. |
| 2004/0167804 A1 | 8/2004 | Simpson et al. |
| 2004/0176984 A1 | 9/2004 | White et al. |
| 2004/0193448 A1 | 9/2004 | Woodbridge et al. |
| 2004/0195264 A1 | 10/2004 | Mastbrook |
| 2004/0220832 A1* | 11/2004 | Moll ............ G06Q 40/08 705/2 |
| 2004/0260478 A1 | 12/2004 | Schwamm |
| 2004/0261037 A1 | 12/2004 | Ording et al. |
| 2005/0021369 A1 | 1/2005 | Cohen |
| 2005/0055242 A1 | 3/2005 | Bello et al. |

(56) References Cited

U.S. PATENT DOCUMENTS

| | | |
|---|---|---|
| 2005/0059163 A1 | 3/2005 | Dastane et al. |
| 2005/0073908 A1 | 4/2005 | Bibbo et al. |
| 2005/0081164 A1 | 4/2005 | Hama et al. |
| 2005/0092373 A1 | 5/2005 | Schafer et al. |
| 2005/0108057 A1 | 5/2005 | Cohen |
| 2005/0139515 A1 | 6/2005 | Gu et al. |
| 2005/0144044 A1 | 6/2005 | Godschall et al. |
| 2005/0201345 A1 | 9/2005 | Williamson |
| 2005/0213425 A1 | 9/2005 | Wang et al. |
| 2006/0010400 A1 | 1/2006 | Dehlin et al. |
| 2006/0047538 A1 | 3/2006 | Condurso et al. |
| 2006/0058603 A1 | 3/2006 | Dave et al. |
| 2006/0062238 A1 | 3/2006 | Mahendran et al. |
| 2006/0066581 A1 | 3/2006 | Lyon et al. |
| 2006/0176403 A1 | 8/2006 | Gritton et al. |
| 2006/0190297 A1 | 8/2006 | Glass et al. |
| 2006/0231108 A1 | 10/2006 | Novatzky et al. |
| 2007/0020341 A1 | 1/2007 | Miyata |
| 2007/0040787 A1 | 2/2007 | Saha |
| 2007/0046596 A1 | 3/2007 | Sakakibara et al. |
| 2007/0078878 A1 | 4/2007 | Knable |
| 2007/0091716 A1 | 4/2007 | Zeikus |
| 2007/0112603 A1 | 5/2007 | Kauthen et al. |
| 2007/0125709 A1 | 6/2007 | Nigam |
| 2007/0130287 A1* | 6/2007 | Kumar ............... G16H 40/63 709/217 |
| 2007/0168229 A1 | 7/2007 | Kim |
| 2007/0223877 A1 | 9/2007 | Kuno |
| 2007/0251336 A1 | 11/2007 | Nielsen et al. |
| 2008/0015487 A1 | 1/2008 | Szamosfalvi et al. |
| 2008/0027374 A1 | 1/2008 | Jensen et al. |
| 2008/0097283 A1 | 4/2008 | Plahey |
| 2008/0097550 A1 | 4/2008 | Dicks et al. |
| 2008/0154177 A1 | 6/2008 | Moubayed et al. |
| 2008/0171596 A1 | 7/2008 | Hsu |
| 2008/0268413 A1 | 10/2008 | Leichner |
| 2008/0275721 A1 | 11/2008 | Nagai et al. |
| 2008/0294019 A1 | 11/2008 | Tran |
| 2009/0008331 A1 | 1/2009 | Wilt et al. |
| 2009/0037216 A1 | 2/2009 | Bluemler et al. |
| 2009/0076338 A1* | 3/2009 | Zdeblick ............ G06F 19/3456 600/300 |
| 2009/0076856 A1 | 3/2009 | Darby et al. |
| 2009/0306573 A1* | 12/2009 | Gagner ............... G06F 19/3418 604/5.01 |
| 2010/0010428 A1* | 1/2010 | Yu ......................... A61M 1/28 604/29 |
| 2010/0076398 A1 | 3/2010 | Scheurer et al. |
| 2010/0137693 A1 | 6/2010 | Porras et al. |
| 2010/0302897 A1 | 12/2010 | George et al. |
| 2010/0317602 A1 | 12/2010 | Moore |
| 2011/0105979 A1 | 5/2011 | Schlaeper et al. |
| 2012/0277170 A1 | 11/2012 | Moore |
| 2013/0211206 A1 | 8/2013 | Sands |
| 2018/0369806 A1 | 12/2018 | Behnk |

FOREIGN PATENT DOCUMENTS

| | | |
|---|---|---|
| EP | 2043014 A1 | 4/2009 |
| JP | 2003006331 A | 1/2003 |
| JP | 2008284229 A | 11/2008 |
| KR | 2001-091801 | 10/2001 |
| WO | 1996028086 | 9/1996 |
| WO | 2002007591 | 1/2002 |
| WO | 2004070995 A2 | 8/2004 |
| WO | 2006018555 A1 | 2/2006 |
| WO | 2006020862 A2 | 2/2006 |
| WO | 2006122325 A2 | 11/2006 |
| WO | 2007033600 A1 | 3/2007 |
| WO | 2007035696 A1 | 3/2007 |
| WO | 2007038147 A2 | 4/2007 |
| WO | 2007040963 A2 | 4/2007 |
| WO | 2007040975 A2 | 4/2007 |
| WO | 2007044877 A2 | 4/2007 |
| WO | 2007049163 A2 | 5/2007 |
| WO | 2007049253 A2 | 5/2007 |
| WO | 2007053683 A2 | 5/2007 |
| WO | 2007120904 A2 | 10/2007 |
| WO | 2007126360 A1 | 11/2007 |
| WO | 2008008281 A2 | 1/2008 |
| WO | 2008110674 A1 | 9/2008 |
| WO | 2009002620 A1 | 12/2008 |

OTHER PUBLICATIONS

[No Author Listed] Nintendo, "Wii Fit Plus" 34 pages. 2009.

[No Author Listed] Nintendo, "Wii Opertations Manual" 2011. 17 pages.

[No Author Listed] US NIH, "MedlinePlus-Hypotension" updated Feb. 20, 2011. 4 pages.

[No Author] Dialysis data acquisition and management system: Finesse® Professional. Fresenius Medical Care. Product information sheet. 2002, 2 pages.

[No Author] Dialysis data management system FinProDB: Finesse® Professional Database. Fresenius Medical Care. Product informationsheet. 2004, 2 pages.

[No Author] Exalis: Dialysis data management tool. Gambro Lundia AB. Product information sheet. Jun. 2002, 8 pages.

[No Author] Finesse® HomeHemo Dialysis (TI 1025 e, v2.0l). Medvision AG. Product information sheet. 2004, 6 pages.

[No Author] Finesse®. Fresenius Medical Care. Retrieved Jun. 17, 2009 from http://fmc.intra.fresenius.de.2008, 2 pages.

[No Author] Therapy Data Management System: Data acquisition, data management and quality assurance as an integrated solution. Fresenius Medical Care. Product information sheet. 2007, 12 pages.

Anonymous: "Interactive Hospital Menus Go Prime Time" Internet Article. Dietary Manager Magazine, [Online] Apr. 2007 (Apr. 2007), pp. 29-31, XP002505453 Retrieved from the Internet: URL: http://www.dmaonline.org/Publications/articles/2007-04-Interactive.pdf [retrieved on Nov. 25, 2008].

Anonymous: "PatientLife:)System TM your comprehensive solution for patient-centered care" Internet Article. Brochure. Getwellnetwork, Inc., [Online] Mar. 18, 2006 (Mar. 18, 2006), pp. 1-6, XP002505452 Retrieved from the Internet: URL:http://web.archive.org/web/20060318175409/http://www.getwellnetwork.com/pdfs/GWNProductBrochure.pdf [retrieved on Nov. 25, 2008].

Bausch et al. "Physiological responses while playing Nintendo Wii Sports." Journal of Undergraduate Kinesiology Research May 2, 2008, vol. 3, p. 19-25.

Cowling et al., "Hypotension in the PACU: an Algorithmic Approach" Jun. 2002 Journal of PeriAnesthesia Nursing vol. 17, No. 3. p. 159-63.

European Search Report, EP Application No. 08164693/, dated Dec. 10, 2008.

Intel 510k Summary, Jun. 27, 2008.

International Search Report dated Jul. 23, 2007, for Application No. PCT/US2006/42650 (11 pages).

Nakamoto, Telemedicine System for Patients on Continuous Ambulatory Peritoneal Dialysis, Peritoneal Dialysis International, vol. 27, 2007.

NHS Lothian Implements Intels Personal Health System to Manage Patients with Chronic Conditions, Intel, Feb. 24, 2009.

Schneider, Jon "Jon Schneiders Tech Blog" Feb. 8, 2009. 4 pages.

Hansen, Susan "Dialysis Procedures—Initiation, Monitoring, Discontinuing" NANT 26th Annual National Symposium, Feb. 10-12, 2009.

Nintendo, "Wii Opertations Manual" 2011.

Fresenius Medical Care, "Dialysis Products" 2008.

Cowling et al., "Hypotension in the PACU: An Algorithmic Approach" 2002 Journal of PeriAnesthesia Nursing vol. 17, No. 3.

US NIH, "MedlinePlus—Hypotension" updated Feb. 20, 2011.

Schneider, Jon "Jon Schneiders Tech Blog" Feb. 8, 2009.

Bausch et al. "Physiological responses while playing Nintendo Wii Sports" Journal of Undergraduate Kinesiology Research May 2, 2008, vol. 3.

* cited by examiner

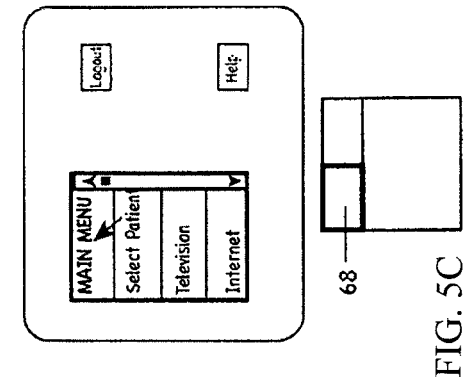
FIG. 5A
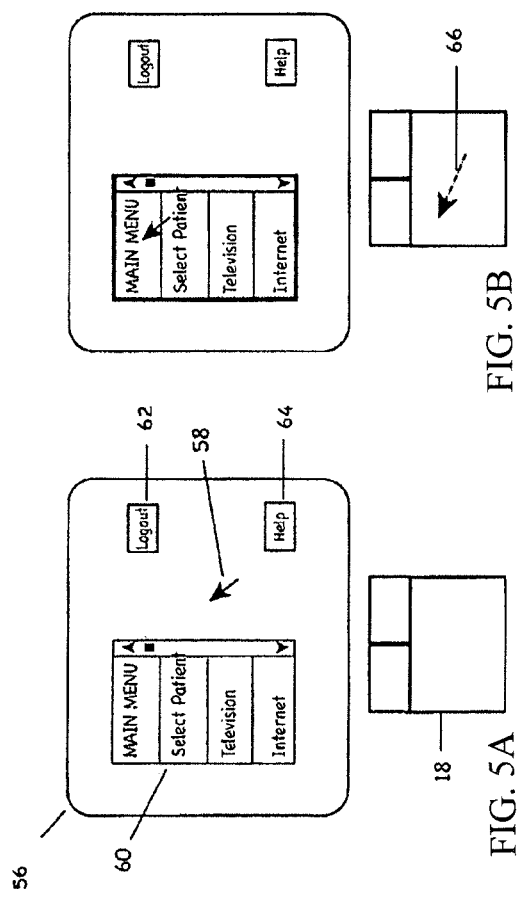
FIG. 5B
FIG. 5C
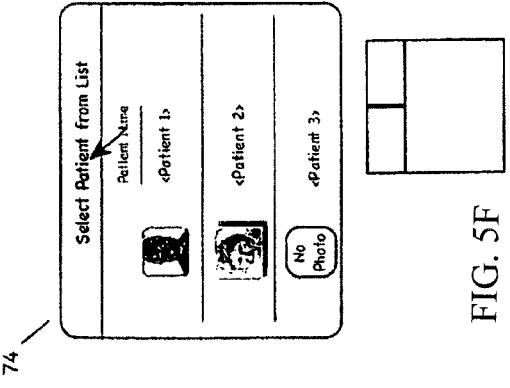
FIG. 5D
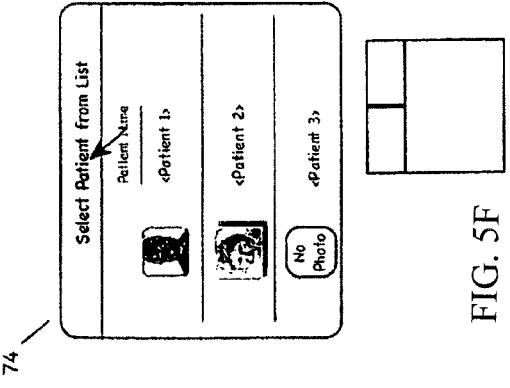
FIG. 5E
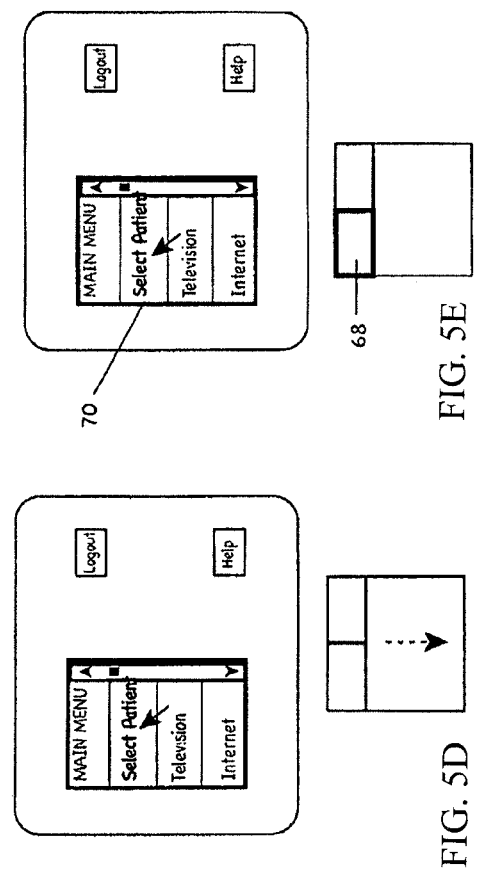
FIG. 5F

REMOTE INTERFACING WITH A NETWORKED DIALYSIS SYSTEM

CROSS REFERENCE TO RELATED APPLICATIONS

The present application is a continuation of U.S. application Ser. No. 14/190,962, filed Feb. 26, 2014, which is a divisional of U.S. application Ser. No. 12/355,082, filed Jan. 16, 2009 and issued on Apr. 15, 2014 as U.S. Pat. No. 8,698,741, both entitled "METHODS AND APPARATUS FOR MEDICAL DEVICE CURSOR CONTROL AND TOUCHPAD-BASED NAVIGATION," each application of which is hereby incorporated by reference in its entirety.

BACKGROUND OF THE INVENTION

The invention pertains to medical treatment apparatus and methods and, more particularly, to user interfaces therefor. The invention has application in facilitating user interaction with medical apparatus, such as peritoneal dialysis equipment, by way of non-limiting example.

Today, computers can be found nearly everywhere, including in medical equipment at hospitals, laboratories, and even patients' bedsides. The equipment typically includes, in addition to a central processing unit and monitor, a keyboard, mouse and/or other input devices. The latter allow users (e.g., doctors, nurses, patient care technicians, other health care providers, and/or patients themselves) to enter data and/or to control the medical equipment—often, by selecting from among options displayed on the monitor. Mice and keyboards, in particular, have fallen out of favor in healthcare settings due to recent studies implicating them in the spread of disease. They are increasingly being replaced with touchpads and touch screens, which can be cleaned more easily.

There are a number of challenges in designing computerized medical equipment, not the least of which is integrating keyboards, mice, touchpads, or other input devices with displays (on the monitor) to form "user interfaces" that can be readily understood and efficiently operated. A good user interface, for example, must respond to user input keyboard taps or mouse motions) quickly and accurately. Often a pointer or cursor, that is, a graphic shaped like an arrowhead, plus sign, pointing finger, an "I" bar, or the like identifying the target of user input, is instrumental in providing that feedback. Yet this raises a further challenge: integrating keyboards, mice, touchpads (or other input devices), and displays with the cursor. Various solutions addressing these issues (for example, hardware-based cursor control circuitry) have been suggested in the prior art, but these can be costly and/or limiting.

An object of the invention is to provide improved medical treatment apparatus and methods. Related objects provide such apparatus and methods as can be used in a wide variety of medical settings, from laboratory to bedside.

A further object of the invention is to provide such apparatus and methods as facilitate integration of computers with medical equipment. A still further object of the invention is to provide such apparatus and methods as facilitate integration of input devices with such computers and/or medical equipment.

A still further object of the invention is to provide such apparatus and methods as facilitate display of a user interface.

Yet a still further object of the invention is to provide such apparatus and methods as can be readily implemented and used on a range of available platforms.

SUMMARY OF THE INVENTION

The foregoing objects are among those attained by the invention which provides, in some aspects, medical apparatus with software-based cursor control. This can be used, by way of non-limiting example, as part of a graphical user interface by which doctors, nurses, patient care technicians, other health care providers, and/or patients enter data into and/or control the apparatus and/or associated medical equipment.

Medical apparatus according to one such aspect of the invention includes a user interface system with a main image subsystem, a cursor subsystem, a monitor, graphics logic, and a video memory. The main image subsystem stores, e.g., to the video memory, data structures and/or other information (collectively, "screen-representative information") representing graphics and/or text to be displayed on the monitor. The cursor subsystem modifies at least a portion of the screen-representative information in the video memory, replacing it with data structures and/or other information (collectively, "cursor-representative information") representing a cursor graphic (e.g., an icon representing an arrowhead) to be displayed on the monitor. The graphics logic drives screen- and/or cursor-representative information from the video memory to the monitor for display of the graphics and/or text represented thereby. The cursor subsystem responds to a change in cursor-representative information previously written by it to the video memory by re-writing that information to the video memory.

Related aspects of the invention provide medical apparatus as described above in which, in connection with storing screen-representative information to the video memory, the main image subsystem changes (e.g., overwrites) cursor-representative information previously written by the cursor subsystem to that memory.

Further related aspects of the invention provide medical apparatus as described above in which (i) the cursor-representative information comprises bit patterns representing the cursor to be displayed on the monitor, and (ii) the cursor subsystem writes those bit patterns to the video memory at a location corresponding to that at which the cursor is to be displayed on the monitor.

Still further related aspects of the invention provide medical apparatus as described above in which (i) the screen-representative information comprises bit patterns representing the graphics and/or text to be displayed on the monitor, and (ii) the main image subsystem writes those bit patterns to the video memory at one or more locations corresponding to those at which such graphics and/or text are to be displayed.

Yet still further related aspects of the invention provide medical apparatus as described above in which the cursor subsystem detects a change in a bit pattern previously written by it to the video memory and responds to such by re-writing that bit pattern.

In a related aspect of the invention, the cursor-representative bit patterns written to the video memory by the cursor subsystem of medical apparatus as described above are distinguishable from the graphics- and/or text-representative bit patterns written to that memory by the main image subsystem. For, example, the bit patterns written by the cursor subsystem can comprise one or more colors, numerical ranges and/or sequences not typical to or represented by the bit patterns written by the main image subsystem.

In a further related aspect of the invention, the cursor subsystem of medical apparatus as described above can test the values in the video memory in order to detect a change in a bit pattern previously written by it to the video memory. Such testing can be for, by way of example, colors, numerical ranges and/or sequences of the type written by the cursor subsystem (but not typically by the main image subsystem) to the video memory.

Further aspects of the invention provide medical apparatus as described above in which, in connection with modifying at least a portion of the screen-representative information in the video memory, the cursor subsystem stores to a buffer a portion of the screen-representative information that it replaces with cursor-representative information. For example, in aspects of the invention, wherein the screen- and cursor-representative information comprise bit patterns, the cursor subsystem can, for example, (i) write cursor-representative bit patterns to the video memory at a location corresponding to that at which a cursor us to be displayed on the monitor, and (ii) write graphics- and/or text-representative bit patterns previously in that location of the video memory to the buffer.

In other aspects, the invention provides medical apparatus, e.g., of the type described above, that additionally includes a touchpad and touchpad subsystem. According to these aspects, the main image subsystem stores to the video memory screen-representative information for a user interface that includes text and/or graphics representing buttons, widgets (e.g., dialog boxes, dials, numeric digit wheels, alpha character wheels, check boxes, etc.) and/or other items (e.g., menus) for display at locations selectable and/or manipulable by a user (i.e., "hot spots"). The touchpad subsystem identifies gestures on the touchpad and generates notifications in response to them. Those gestures include at least a contacting touch of length (e.g., a linear or curvilinear swipe) and may additionally include a tap or point touch (i.e., a contacting touch of substantially no length). The notifications can indicate the gesture type, location, magnitude and/or direction.

In further accord with these aspects of the invention, an application (or other functionality, e.g., middleware/software) that defines the user interface responds to those notifications by highlighting (or activating) a hot spot. That application (or other functionality) can, instead or in addition, treat the notifications as indicative of substantive user input, e.g., numeric, alpha or other value selections based on the type of activated hot spot, the user-selectable values associated with it, the gesture type, location, magnitude and/or direction. According to related aspects of the invention, the cursor subsystem can be coupled to the application and can receive from it locations of hot spots onto which a cursor is to be overlaid for display on the monitor.

By way of example, in medical apparatus according to these aspects of the invention, the touchpad subsystem can respond to a user's upward swipe of the touchpad by sending a corresponding notification to application software that defines a user interface currently displayed on the monitor. The application (or other functionality) can, in turn, determine that a new hot spot should be activated—e.g., one just above a currently activated hot spot. The application can generate a corresponding application window, with that new hot spot highlighted, for rendering on the monitor by the main image subsystem and graphics logic. By way of further example, the application can respond to subsequent notification, from the touchpad subsystem, of a user's downward swipe on the touchpad by selecting a first user-selectable item in the currently selected hot spot—both generating a new application window with that item selected and taking a value associated with that item as an input. By way of further example, in the case of an activated widget that displays an alpha character, a digit or other enumerated value (e.g., a word from a dictionary, a value from a list of permissible values, and so forth), the application can respond to a swipe on the touchpad by incrementing or decrementing that displayed value (depending on the direction of the swipe) and accepting the finally selected value (as indicated, e.g., by a confirmatory tap or a cessation of motion) as an input.

Yet still further aspects of the invention provide medical apparatus as described above in which the cursor subsystem can effect display of a cursor graphic at cursor display position newly determined as a function of a current cursor display position and a gesture type, location, magnitude and direction. Systems according to this aspect of the invention can effect display of such a graphic, e.g., by modifying video memory in the manner discussed above.

Further aspects of the invention provide systems employing combinations of the features described above.

Yet still further aspects of the invention provide methods for operation of medical apparatus with a (graphical) user interface paralleling the operations described above.

These and other aspects of the invention are evident in the drawings and in the description that follows.

BRIEF DESCRIPTION OF THE DRAWINGS

A more complete understanding of the invention may be attained by reference to the drawings, in which:

FIGS. 5A, 5B, 5C, 5D, 5E, 5F, 6A, 6B, 6C, 6D, 6E, 6F, 7A, 7B, 7C, 7D, 7E, 8A, 8B, 8C, and 8D illustrate hotspot selection via a touchpad in a system of the type shown in FIG. 1.

DETAILED DESCRIPTION OF THE ILLUSTRATED EMBODIMENT

Figure 1:
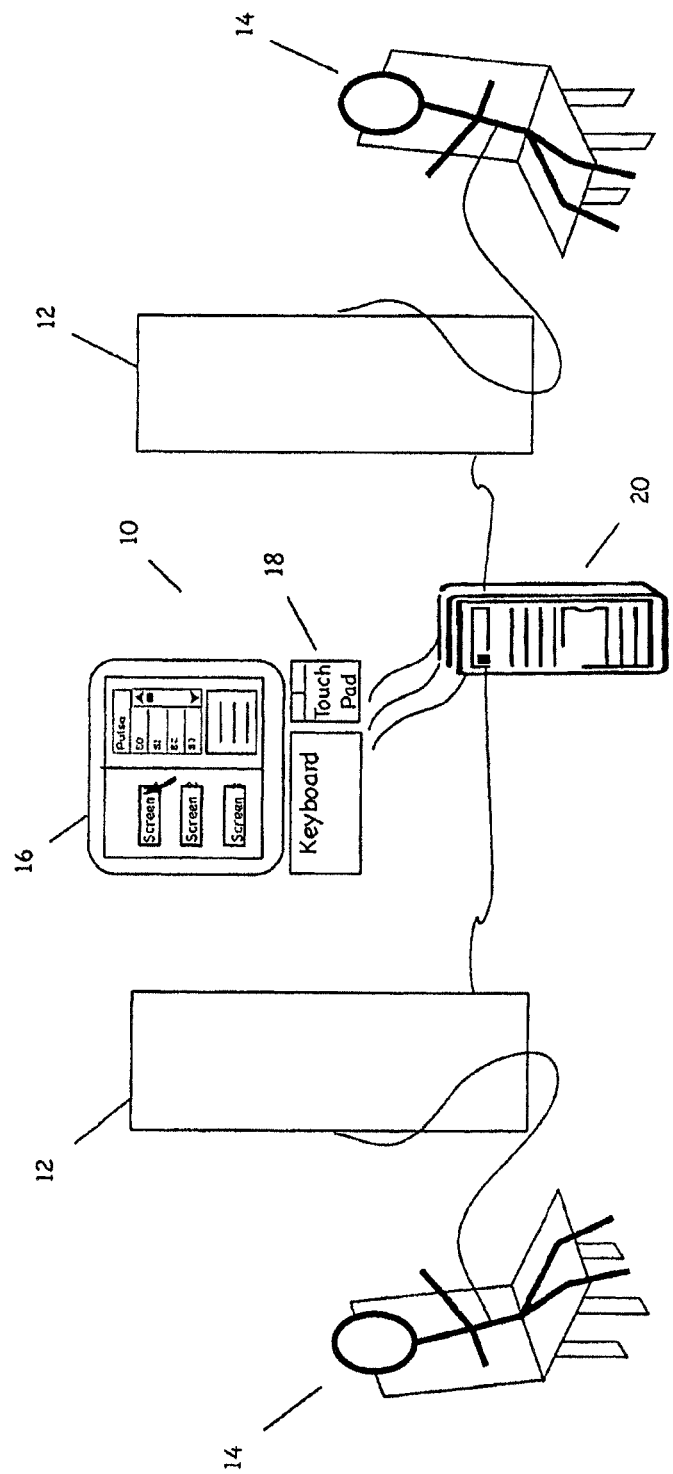
FIG. 1 depicts a patient treatment system according to one practice of the invention.

FIG. 1 depicts a medical apparatus according to one practice of the invention, as well as an environment of the type in which the invention can be practiced. The apparatus 10 shown in that figure and described below, by way of non-limiting example, is a data entry station, though it will be appreciated that in other embodiments apparatus 10 may comprise any of a variety of other apparatus for controlling, collecting data from and/or interfacing with medical equipment.

Illustrated data entry station 10 is used in connection with medical treatment apparatus 12 (here, dialysis equipment) to facilitate treatment of patients 14 and, more particularly, to facilitate data entry by doctors, nurses, patient care technicians, other health care providers, and/or patients, collection of data from apparatus 12, and/or monitoring and control of that apparatus 12. The device 10 comprises a digital data processor 20, a monitor 16, and a touchpad 18 or other input device (e.g., keyboard, mouse and/or touchscreen). Although two apparatus 12 are shown, those skilled in the art will appreciate that the data entry station 10 may support fewer or more than two such apparatus and, indeed, may be used without such apparatus 12—or may be incorporated directly into it.

In the illustrated embodiment, monitor 16 displays information relating to medical treatment apparatus 12, treatment of patient 14 and/or other aspects of patient care, all under the control of a digital data processor 20. This includes, by way of non-limiting example, graphics and/or text generated by software applications executing on the digital data processor 20 (e.g., in connection with data or other information generated by apparatus 12), as well as graphics and/or text defining a "user interface" generated by such software applications or otherwise. That user interface is used by a doctor, nurse, patient care technician, other health care provider, patient or other user to interact with the station 10 and/or apparatus 12 for purposes, by way of non-limiting example, of reviewing patient care information, entering data, issuing commands, and so forth. As used in this paragraph and throughout, "graphics" refers to images and other visual display elements.

Monitor 16 of the illustrated embodiment comprises a liquid crystal display, cathode ray display, plasma display, light emitting diode display, or other display of the type commercially available in the marketplace, albeit operated in accord with the teachings hereof. In other embodiments, information displayed on monitor 16 can be output, instead or in addition, to a monitor provided with apparatus 12, to a printer (not shown) or other output device (local or remote) via a wired, wireless, networked communications link.

Illustrated touchpad 18 generates signals indicative of a user's touch. The touchpad 18 comprises a conventional such device of the type generally available in the marketplace, albeit operated in accord with the teachings hereof. In other embodiments, touchpad 18 can be supplemented with or supplanted by other input devices, such as a touchscreen or mouse, for user input. For sake of convenience, the teachings that follow assume that user input is provided (at least in part) via touchpad 18; however, it will be appreciated that such teachings are equally applicable to input via touchscreen, mouse, and so forth.

Illustrated digital data processor 20 controls the data entry station 10, e.g., interfacing with treatment apparatus 12, collecting and/or analyzing patient data, generating information including the aforementioned user interface for display on the monitor 16, accepting input from the user (including via touchpad 18), storing and/or transmitting data (and/or other information) to databases and/or remote systems, and so forth. The digital data processor 20 of the illustrated embodiment comprises a workstation or personal computer of the type generally available in the marketplace, albeit as adapted in accord with the teachings hereof. In other embodiments, it may comprise an embedded processor, workstation, minicomputer, mainframe, or other digital data processing device of the type known in the art, again, as adapted in accord with the teachings hereof.

The digital data processor 20 may be a stand alone device as shown in the drawing, or may be integral to one or more other components of the illustrated system, e.g., the monitor 16 and/or medical treatment apparatus 12. It may, moreover, be coupled for communication with the monitor 16 and touchpad 18 via wireless connection (e.g., BlueTooth, 802.1x, or otherwise), wired connection (e.g., Ethernet or backplane bus) or otherwise, all in the conventional manner known in the art.

Figure 2:
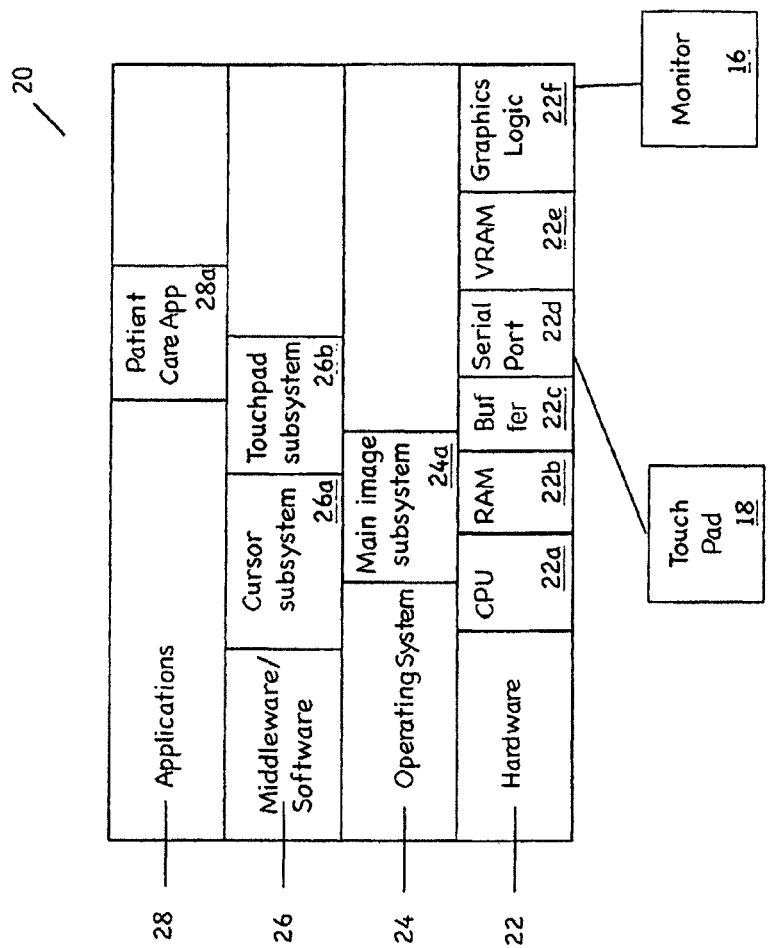
FIG. 2 depicts functional elements of a system of the type shown in FIG. 1.

FIG. 2 illustrates the make-up of digital data processor 20 according to one practice of the invention. Illustrated device 20 generally comprises hardware 22, operating system 24, middleware/software 26, and applications 28, configured and operated in the conventional manner known in the art as adapted in accord with the teachings hereof.

Hardware 22 of the illustrated embodiment comprises central processing unit (CPU) 22*a*, random access memory 22*b*, poll 22*d* (to which touchpad 18 or other input device(s) is/are coupled), video memory 22*e*, and a graphics logic 22*f* (to which monitor 16 or other output device(s) is/are coupled). These comprise conventional components of such type known in the art for use in digital data processor 20, configured and operated in the conventional manner known in the art, albeit, as adapted in accord with the teachings hereof. Thus, by way of non-limiting example, graphics logic 22*f* comprises a graphics card, graphics chip set, graphics processing unit and/or other functionality of the type known in the art (as adapted in accord with the teachings hereof) capable of driving bit patterns or other representations generated by applications 28, middleware/software 26 and/or operating system 24*a* to monitor 16 for display thereon. Illustrated hardware 22 additionally includes buffer 22*c* (which is occasionally referred to herein as a "behind-the-cursor array," in reference to the software structure that maps onto buffer 22*c*) which may be implemented in RAM 22*b*, VRAM 22*e*, or other memory.

The components of hardware section 22 illustrated in FIG. 2 are by way of example only; other embodiments may incorporate other components, instead or in addition. Moreover, in other embodiments, one or more functions performed by the hardware components may be performed in software, firmware and/or vice versa.

Operating system 24 manages and coordinates execution of software and hardware 22 of a digital data processor 20, in the conventional manner known in the art (as adapted in accord with the teachings hereof). The operating system 24 comprises Unix, Microsoft Windows, Mac OS X, Linux, Solaris, or other operating system software of the type known in the art, as adapted in accord with the teachings hereof. In alternate embodiments, functionality of the operating system 24 may be embodied in one or more other hardware and/or software components.

In the illustrated embodiment, operating system 24 includes, inter alia, main image subsystem 24*a*, which is responsible for effecting storage, e.g., to video memory 22*e*, of data structures and/or other information (collectively, "screen-representative information") representing the screens generated by applications 28, middleware/software 26 and/or (other) operating system utilities to video memory 22*e*, whence graphics logic 22*f* drives it to monitor 16 (or other output device) for display.

The data structures and/or other information that make up the screen-representative information includes, as is conventional in the art, codes or bit patterns (collectively, "bit patterns") that govern the display characteristics of the text and graphics—or portions thereof (e.g., pixels)—that make up the application windows as displayed on monitor 16. Those characteristics include, again, as is conventional in the art, color, intensity, and so forth. In the illustrated embodiment, bit patterns included in screen-representative information can, for example, cover the conventional gamut of colors generated by applications programs 28, e.g., 32-bit color, 16-bit color, 8-bit color, and so forth.

Main image subsystem 24a of the illustrated embodiment comprises conventional software—such as a "windowing" subsystem—of the type known in the art (as adapted in accord with the teachings hereof) for providing windowing functionality. Though shown, here, as part of operating system 24, in other embodiments, main image subsystem 24a may comprise components within the middleware/software 26, applications 28 and/or hardware 22.

In the illustrated embodiment, middleware/software 26 comprise software modules that facilitate execution and implementation of functions requested and/or performed by applications 28 (as well, potentially, by operating system 24). This can include, by way of non-limiting example, graphics, mathematical/statistical and other runtime libraries of the type commercially available in the marketplace. In the illustrated embodiment, this includes a touchpad subsystem 26b and a cursor subsystem 26a, as further discussed below and elsewhere herein. In alternative embodiments, the functions implemented by middleware/software 26 can be implemented directly in applications 28, operating system 24, as web services on remote digital data processing systems to which digital data processor 20 is coupled, and/or in hardware 22.

Applications 28, including exemplary application 28a, comprise conventional software of the type known in the art for use in health care environments, including, by way of non-limiting example, software for interfacing with treatment apparatus 12, collecting and/or analyzing patient data, generating information (including the aforementioned user interface), accepting input from the user, storing and/or transmitting data (and/or other information) to databases and/or remote computer systems, and so forth—e.g., with the assistance of the middleware/software 26, operating system 24 and hardware 22.

To this end, the application 28a (by way of example), generates windows ("application windows") or screens in the conventional manner known in the all (as adapted in accord with the teachings hereof) with information—e.g., text and graphics—to be displayed on monitor 16. These screens can include information pertaining to apparatus 12, the patient, his/her condition and/or treatment, and so forth. They can, in addition or instead, include buttons, widgets (e.g., dialog boxes, dials, numeric digit wheels, alpha character wheels, check boxes) and/or other items (e.g., menus) for display at locations selectable and/or manipulable by a user (i.e., "hot spots") in the conventional manner of a user interface and, more particularly (by way of non-limiting example), a graphical user interface ("GUI"), again, as adapted in accord with the teachings hereof. As noted above, the main image subsystem 24a stores screen-representative information representing the screens generated by application 28a to VRAM 22e, whence the graphics logic 22f drives it to monitor 16.

Cursor Subsystem

The cursor subsystem 26a comprises software that effects display of a cursor—e.g., a visual element shaped like an arrowhead, plus sign, pointing finger, an "I" bar, or the like—on the monitor. Unlike prior-art hardware-based systems, the cursor subsystem 26a advantageously does this by "writing over," yet, retaining, screen-representative information (representing text and/or graphics generated by application 28) in the video memory—and, more particularly, by (i) replacing screen-representative information in that memory 22e with data structures and/or other information (collectively, "cursor-representative information") representing a cursor graphic to be displayed on the monitor, and (ii) caching the replaced screen-representative information so that it can be restored if/when the cursor is subsequently repositioned.

As with the screen-representative information, the data structures and/or other information that make up the cursor-representative information include hit patterns that govern the display characteristics of the cursor as displayed on monitor 16. Those characteristics include, again, as is conventional in the art color, intensity, and so forth. In some embodiments, by way of non-limiting example, bit patterns included in cursor-representative information represent colors falling outside the gamut of colors generated by applications programs 28, e.g., outside the conventional 32-bit color, 16-bit color, and 8-bit color gamuts, and so forth. Alternatively, in some embodiments, bit patterns included in cursor-representative information represent colors fall within the general color gamut utilized by the applications program 28, but represent, unique colors or color combinations within that gamut. More generally, the cursor subsystem 26a generates and stores to memory 22e cursor-representative signals including bit patterns indicative of color(s), numerical ranges and/or sequences not typical to or represented by the bit patterns written by the main image subsystem on behalf of the applications program 28a.

Cursor Positioning and Repositioning

In the illustrated embodiment, the subsystem 26a modifies memory 22e directly and/or using componentry (of the operating system 24 and/or middleware/software 26) other than the main image subsystem 24a. However, in other embodiments, subsystem 26a employs subsystem 24a, instead or in addition, to so modify memory 22e. As above, graphics logic 22f drives the contents of the video memory 22e, here, including both the screen-representative information and the cursor-representative information, to the monitor 16 in order to effect a display that includes a cursor in addition to the screens generated by the application 28a.

Subsystem 26a does not replace all screen-representative information in the memory 22e with cursor-representative information but, rather, only that disposed at a location (in video memory 22e) corresponding to that at which the cursor is to be displayed on the monitor. At initiation, e.g., boot-up of application 28a, subsystem 26a effects display of the cursor at a default location, e.g., the center or corner of a most-recently generated application window. Typically, the subsystem 26a effects repositioning of the cursor in response to user touch/movement of the touchpad 18, as detailed more fully below; although, it can also effect a reset of the cursor position in absence of such touch/movement, e.g., following the close of an application window, activation of GUI widgets (or hotspots), and so forth.

Regardless, the subsystem 26a "caches" the screen-representative information (representing text or graphics generated by the main image subsystem 26b) before replacing it in memory 22e with cursor-representative information. It does this by storing the screen-representative to the behind-the-cursor array (or buffer) 22C. That array (which as noted above, can map to storage forming part of RAM 22b, VRAM 22e, or other memory) is sized sufficiently to hold that information—optionally, by way of non-limiting example, along with current and/or prior cursor positions, which can be stored relative to the VRAM 22e indexing scheme or the corresponding reference frame (e.g., coordinate system) of the monitor 16.

By caching the screen-representative information, the subsystem 26a can restore that information in VRAM 22e when the cursor is repositioned, e.g., in response to user touch/movement of the touchpad 18, following the close of an application window, activation of GUI widgets (or hotspots), and so forth. This has the practical effect of restoring on monitor 16 text or graphics that had been generated by the application 28a (and written to VRAM 22e by the main image subsystem 24a) and that "written over" by the cursor subsystem 26a.

Figure 3:
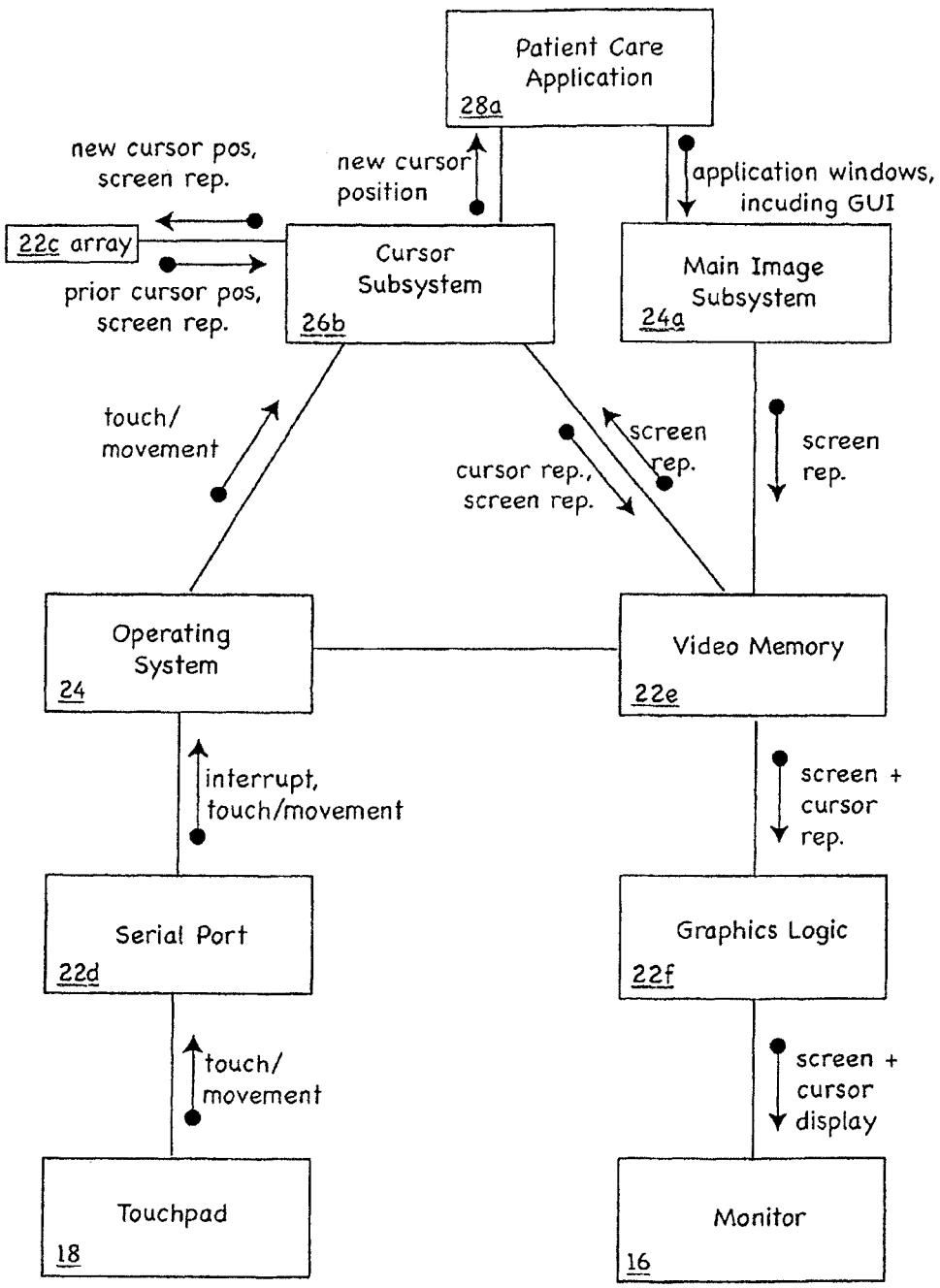
FIG. 3 is a data-flow diagram illustrating the flow of data and control signals in a system of the type shown in FIG. 1 for purposes of cursor display.

FIG. 3 is a data-flow diagram depicting, by way of non-limiting example, a manner in which the cursor subsystem 26a is notified of such repositioning and the actions effected by it in response. Particularly, as shown in that drawing, a user of data entry station 10 effects movement of the cursor displayed on monitor 16 by touching and/or moving his/her finger on the touchpad 18 (or other device) in the conventional manner known in the art, as adapted in accord with the teachings hereof. This can be in connection with setting or altering a target of input, pointing to region of interest, or otherwise. The touchpad IS responds by generating signals indicative of that touch/movement for input to serial port 22d, which in turn generates an interrupt for application to CPU 22a along with the touch/movement information—all in the conventional manner known in the art. Operating system 24 notifies cursor subsystem 26a of the touchpad activity and makes that touch/movement information available to it. This can be effected, by way of non-limiting example, by interrupt handling-code that comprises and/or invokes the cursor subsystem 26a and that stores the touch/movement information to memory for use by it. Though not shown in FIG. 3, it will he appreciated that cursor subsystem 26a can he notified of cursor repositioning in other ways and/or via different mechanisms (e.g., following the close of an application window, display of GUI widgets, and so forth).

Upon notification of cursor repositioning, cursor subsystem 26a assumes or calculates a new cursor display position based on the touch/movement information supplied to it by the operating system 24 and/or the prior cursor position (as stored, for example, in array/buffer 22c). Calculation, where necessary, can include by way of non-limiting example mapping touchpad coordinates to the VRAM 22e indexing scheme and/or corresponding reference frame (e.g., coordinate system) of the monitor 16. Where the user's motion is a "swipe" or other gesture, such calculation can also include by way of further non-limiting example, extrapolating a desired new cursor position from a prior cursor position and a position/magnitude/direction of the gesture—though, in the illustrated embodiment, the cursor subsystem relies on application 28a to define new cursor position following a swipe or other such gesture, as described below. In the illustrated embodiment, the cursor subsystem 26a stores the newly determined cursor position to array/buffer 22c, as noted in FIG. 3.

As evident in the discussion above, upon determination of a new cursor position, the cursor subsystem 26a restores to VRAM 22e screen-representative information cached to array/buffer 22c for the prior cursor position. This, as noted, has the practical effect of restoring on monitor 16 text or graphics that had previously been "written over" by the cursor subsystem. At the same time, the cursor subsystem effects display of the cursor at the new cursor location via the methodology described above, e.g., by replacing screen-representative information in VRAM 22e at locations corresponding to the new cursor position with cursor-representative information and caching that screen-representative position to array/buffer 22c.

Cursor Refreshing

Main image subsystem 24a and cursor subsystem 26a of the illustrated embodiment operate independently, or relatively so, vis-a-vis modification of VRAM 22e and, thereby, displays on monitor 16. Thus, as discussed in the prior section, subsystem 26a overwrites, yet, retains, screen-representative information from subsystem 24a with cursor-representative information in order to effect display of a cursor at user- or application-designated position).

As a further consequence of this (relative) independence, subsystem 24a can overwrite cursor-representative information from subsystem 26a with screen-representative information, e.g., in response to application windows or screens generated by application 28a in the normal of its operation. However, unlike the cursor subsystem 26a, main image subsystem 24a of the illustrated embodiment need not retain the cursor-representative information it overwrites. This facilitates use of conventional applications software 28 in device 10 and, more particularly, on digital data processor 20.

To prevent this action of the main image subsystem 24a from eliminating a stationary cursor from displaying on monitor 16, cursor subsystem 26a periodically tests VRAM 22e to determine whether cursor-representative information still exists at the expected and current cursor location in VRAM, if not, the subsystem 26a re-effects display of the cursor that location via the methodology described above, e.g., by replacing screen-representative information in VRAM 22e at that location with cursor-representative information. The subsystem 26a can simultaneously cache that screen-representative position to array/buffer 22c; though, unless the main image subsystem 24a has since written new screen-representative information to that location in VRAM 22e, this is not necessary.

In the illustrated embodiment, cursor subsystem 26a preferably tests VRAM 22e for the presence of expected cursor-representative information at intervals sufficiently short that overwriting of that information by main image subsystem 24a will not be detected by—or, at least, not be cognitively perceived by and, at very least, not result in irritation of—users viewing monitor 16. The this end, cursor subsystem 26a preferably tests VRAM 22e and (if necessary) rewrites cursor-representative information to it at the expected cursor location in intervals of under ¼ sec. and, more preferably, under ¹⁄₁₀ sec. and, still more preferably, under ¹⁄₆₀ sec.

To perform this testing, cursor subsystem 26a of the illustrated embodiment relies on differences in the codes or bit patterns (collectively, "bit patterns") that make up cursor-representative information and screen-representative information, respectively. Thus, by way of non-limiting example, in embodiments where screen-representative information written by the main image subsystem 24a to memory 22e include bit patterns indicative of colors within an 8-bit color gamut and where cursor-representative information written by the cursor subsystem 26a to that memory include non-overlapping color(s) within a 16-bit gamut, the subsystem 26a can test for those non-overlapping color(s) to determine the presence or absence of expected cursor-representative information. This is likewise true where, by way of non-limiting example, the bit patterns written by the cursor subsystem 26s (a) fall within the same color gamut as those written by the main image subsystem 24a, but (b) utilize colors not used by the main image subsystem 24a.

Figure 4:
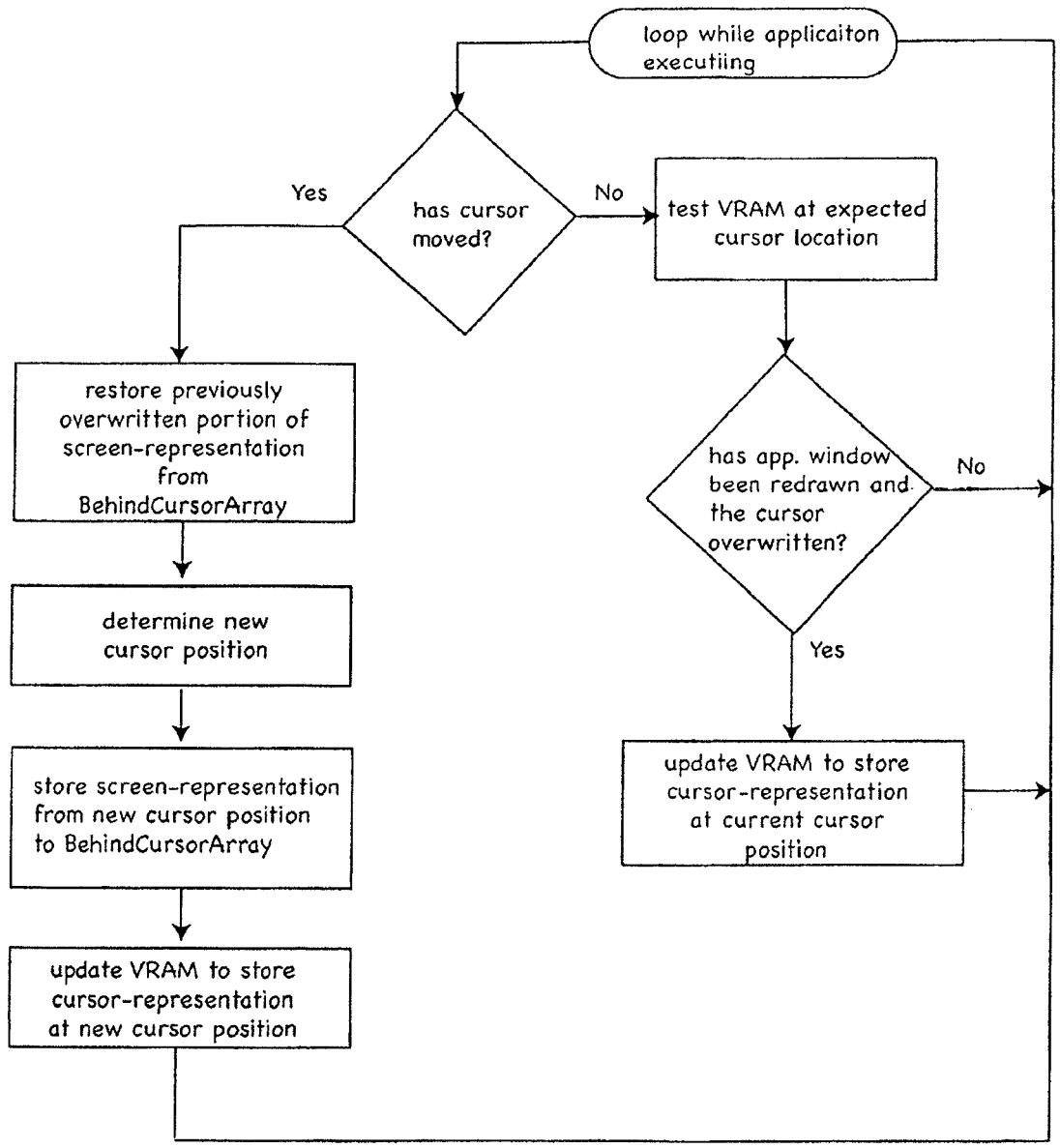
FIG. 4 is a flowchart illustrating a method of cursor repositioning and refreshing in a system of the type shown in FIG. 1.

A further understanding of the operation of the cursor subsystem may be attained by reference to FIG. 4, which is a flowchart illustrating the operations discussed here and in the prior section in regard to cursor repositioning and refreshing. A still further understanding of the operation of the cursor subsystem may be attained by reference the C programming language code that follows illustrating operation of the cursor subsystem according to one practice of the invention:

```
#define NumCursorPixs 97
    U8 BehindCursor[NumCursorPixs];
    const U8 CursorImage[NumCursorPixs][3] = {
    {0, 0,CusorBoader},{1, 0,CusorBoader},
    {0, 1,CusorBoader},{1, 1,CursorFill},
    {2, 1,CusorBoader},
    {0, 2,CusorBoader},{1, 2,CursorFill},
    {2, 2,CursorFill},{3, 2,CusorBoader},
    {0, 3,CusorBoader},{1, 3,CursorFill},
    {2, 3,CursorFill},{3, 3,CursorFill},
    {4, 3,CusorBoader},
    {0, 4,CusorBoader},{1, 4,CursorFill},
    {2, 4,CursorFill},{3, 4,CursorFill},
    {4, 4,CursorFill},{5, 4,CusorBoader},
    {0, 5,CusorBoader},{1,5,CursorFill},
    {2, 5,CursorFill},{3, 5,CursorFill},
    {4, 5,CursorFill},{5, 5,CursorFill},
    {6, 5,CusorBoader},
    {0, 6,CusorBoader},{1, 6,CursorFill},
    {2, 6,CursorFill},{3, 6,CursorFill},
    {4, 6,CursorFill},{5, 6,CursorFill},
    {6, 6,CursorFill},{7, 6,CusorBoader},
    {0, 7,CusorBoader},{1, 7,CursorFill},
    {2, 7,CursorFill},{3, 7,CursorFill},
    {4, 7,CursorFill},{5, 7,CursorFill},
    {6, 7,CursorFill},{7, 7,CursorFill},
    {8, 7,CusorBoader},
    {0, 8,CusorBoader},{1, 8,CursorFill},
    {2, 8,CursorFill},{3, 8,CursorFill},
    {4, 8,CursorFill},{5, 8,CursorFill},
    {6, 8,CursorFill},{7, 8,CursorFill},
    {8, 8,CursorFill},{9, 8,CusorBoader},
    {0, 9,CusorBoader},{1, 9,CursorFill},
    {2, 9,CursorFill},{3, 9,CursorFill},
    {4, 9,CursorFill},{5, 9,CursorFill},
    {6, 9,CusorBoader},{7, 9,CusorBoader},
    {8, 9,CusorBoader},{9, 9,CusorBoader},
    {10, 9,CusorBoader},
    {0,10,CusorBoader},{1,10,CursorFill},
    {2,10,CursorFill},{3,10,CusorBoader},
    {4,10,CursorFill},{5,10,CursorFill},
    {6,10,CusorBoader},
    {0,11,CusorBoader},{1,11,CursorFill},
    {2,11,CusorBoader},{4,11,CusorBoader},
    {5,11,CursorFill},{6,11,CursorFill},
    {7,11,CusorBoader},
    {0,12,CusorBoader},{1,12,CusorBoader},
    {4,12,CusorBoader},{5,12,CursorFill},
    {6,12,CursorFill},{7,12,CusorBoader},
    {0,13,CusorBoader},{5,13,CusorBoader},
    {6,13,CursorFill},{7,13,CursorFill},
    {8,13,CusorBoader},
    {5,14,CusorBoader},{6,14,CursorFill},
    {7,14,CursorFill},{8,14,CusorBoader},
    {6,15,CusorBoader},{7,15,CusorBoader},
    {(8,15,CusorBoader}};
    void EraseCursor(S16 CursorLocX, S16 CursorLocY)
    {
      U32 b, x, y;
      U8 i;
      b = (*(U32*)0x02200850) & 0xFFFFFFF0;
      for (i = 0; i<NumCursorPixs; i++)
      {
         x = CursorLocX + CursorImage[i][0];
         y = ((CursorLocY + CursorImage[i][1]) * 640);
                 //Restore Background
         (*(U8 *)(b + y + x)) = BehindCursor[i];
      }
    } void DrawCursor(void)
{
   U32 b, x, y, s;
   U8 i,c,j;
            //Move to New Position
   CursorLocX += MoveX;
   CursorLocY += MoveY;
            //Check the boundry
   if(CursorLocX >= 630) CursorLocX = 630;
   else if(CursorLocX <= 0) CursorLocX = 0;
   if(CursorLocY >= 460) CursorLocY = 460;
   else if(CursorLocY <= 0) CursorLocY = 0;
   b = (*(U32*)0x02200850) & 0xFFFFFFF0;
   for (i = 0; i<NumCursorPixs; i++)
   {
      x = CursorLocX + CursorImage[i][0];
      y = ((CursorLocY + CursorImage[i][1]) * 640);
            //Cursor moving to new position,
            //Save whole background at new position
      if(MoveX || MoveY)
      {
         BehindCursor[i] = (*(U8 *)(b + y + x));
            //Show Cursor Image at new location
         (*(U8 *)(b + y + x)) = CursorImage[i][2];
      }else
            //Refresh the Cursor image at the
            //current location, only if the image
            //behind the cursor is changed need to be saved
      {
         if(CursorImage[i][2] != (*(U8 *)(b + y + x)))
         {
            BehindCursor[i] = (*(U8 *)(b + y + x));
            (*(U8 *)(b + y + x)) = CursorImage[i][2];
         }
      }
   }
            //Ready for next move
   MoveX = MoveY = 0;
}
void InitCursor(void)
{
   U16 i;
   if(CursorLocX >= 639 || CursorLocY >= 479)
   {
      CursorLocX = 320; CursorLocY = 240;
   }
   MoveX = MoveY = 0;
   for (i = 0; i<NumCursorPixs; i++)
      BehindCursor[i] = Red;
   CursorTimer = 101;
}
void HandleCursor(void)
{
   if((MoveX || MoveY) && !SetToNewTx)
   {
      if(CursorTimer != 101)
            //At the CurrentPosition
         EraseCursor(CursorLocX, CursorLocY);
         SimulateTouch = 2;
         CursorTimer = 0;
   }
   if(CursorTimer < 100)
   {
      DrawCursor( );
   }else if(CursorTimer == 100)
   {
      EraseCursor(CursorLocX, CursorLocY);
      SimulateTouch = 2;
            CursorTimer = 101;
   }
}
```

Touchpad Subsystem

The touchpad subsystem 26b comprises software that identifies gestures by the user on the touchpad 18 and, in response, generates notifications indicative of the type, location (e.g., start and/or end position on the touchpad 18), magnitude and/or direction of the gestures. Those gestures include at least a contacting touch of length (e.g., a linear or curvilinear swipe) and may, optionally, include a tap or point touch (i.e., a contacting touch of substantially no length). The notifications can be used by application 28a and/or the main image subsystem 24a to alter display of an application window—e.g., to highlight a newly activated hot spot and/or to display a value selected by the user via the gesture. The notifications can also be used by the application 28a as indicative of substantive user input, e.g., numeric, alpha or other value selections, based on the type of activated hot spot, the user-selectable values associated with that hot spot, the gesture type, location, magnitude and/or direction. The cursor subsystem 26a can also use such notifications from the touchpad subsystem and/or subsequent resultant notifications from the application 28a to generate a cursor-representative signal for repositioning a cursor on the monitor 16, e.g., within a newly activated hot spot.

FIGS. 5A-5F, 6A-6F, 7A-7E, and 8A-8D depict, by way of non-limiting example, user gestures on touchpad 18 and their effect on a user interface generated by application 28a for display on monitor 16. Each of those figures is in two parts: an upper part depicting the user interface generated by application 28a and driven to the monitor via main image subsystem 24a and graphics logic 221, e.g., as described above; and, a lower pail, depicting user gestures (e.g., swipes and touches) on touchpad 18. Application windows depicted in these figures may include, in addition to the illustrated user interfaces, other text and graphics—not shown, here, for sake of simplicity —generated by application 28a relating to medical treatment apparatus 12, treatment of patient 14 and/or other aspects of patient care, by way of non-limiting example. Like elements of these figures are not labelled with reference numbers to avoid clutter and for sake of simplicity.

Referring to FIG. 5A, by way of example, there is shown an application window 56 of the type generated by application 28a and displayed on monitor 16 with a graphical user interface that includes user selectable and/or manipulable hot spots 60—64, here, representing a menu (60) and two buttons (62, 64). None of those elements are highlighted or activated, as indicated by an absence of boldface type and/or thick lines. A cursor 58 of the type generated by cursor subsystem is also shown, here, in its default position in the center of window 56.

Referring to FIG. 5B, there is shown a user swipe 66 on touchpad 18. Here, the swipe is in an upward left direction. In the illustrated system, such a swipe results in activation one of the hotspots as a function of one or more factors, including: gesture type, location of the gesture on the touchpad, magnitude and/or direction of the gesture, current position of cursor 58, and/or location of the currently activated hotspot, if any. Various embodiments may use fewer or more factors and or may weight these factors differently from one another. As evident in the discussion that follows, for swipe-type gestures, the illustrated embodiment principally weights (i) direction of the gesture, and (ii) current position of cursor 58 and/or location of the currently activated hotspot. Those skilled in the art will appreciate, in view of the teachings hereof, how these and other embodiments may make additional or alternate use of the other factors (aforementioned or otherwise).

Turning back to FIG. 5B, the swipe results in activation of menu 60, since that hotspot is left of the current cursor position. Activation of that hotspot may be indicated in any number of ways in the user interface, when it is regenerated by application 28a following notification of the swipe b) touchpad subsystem 26b. For example, the application 28a may show that hotspot 60 with a bold line about its perimeter, as in the drawing. The application 28a may, instead or in addition, indicate such activation by regenerating the user interface with the hotspot 60 depicted with varied color, intensity and so forth.

In the illustrated system, the swipe also results in repositioning of cursor 58 to a location nearer, e.g., on the perimeter of or within the hotspot 60, as shown. This is effected by action of the cursor subsystem 26a in response to notification of the swipe from the touchpad subsystem 26b and/or the application 28a. Similar cursor repositioning is generally shown in applicable ones of FIGS. 5C-8D, with little comment in the text that follows.

Referring to FIG. 5C, a user tap on touchpad 18 and/or one if its attendant buttons (here, left touchpad button 68) confirms selection of the hotspot 60. Here, that tap is conveyed by a notification from the touchpad subsystem 26b to the application 28a, which can again regenerate the user interface with further variation—e.g., further signifying to the user that the hotspot has been activated. Here, that further variation is the boldface display of the menu title ("Main Menu"), though, in other embodiments, other indications may be used instead or in addition. Though the tap shown in FIG. 5c is made on attendant button 68 (as is the case with similar taps shown in applicable ones of FIGS. 5D-8D), it will be appreciated that those taps can be made directly on touchpad 18, instead or in addition.

Referring to FIG. 5D, there is shown a further user swipe 66 on touchpad 18, here, in a downward direction. With hotspot 60 already activated, this swipe results in selection of the nearest user-selectable value of the hotspot from (a) the current position of cursor 58, and/or (b) a previous selected value (if any) in the direction indicated by the swipe. Here, the swipe results in selection of the topmost menu option ("Select Patient"), since that is the nearest user-selectable value in the downward direction from the cursor and from the title that was activated in connection with the actions shown in FIG. 5C. As above, selection of the value may be indicated in any number of ways in the user interface, when it is regenerated by application 28a following notification of the swipe by touchpad subsystem 26b. For example, the application 28a may show that selection with boldface type, varied color, intensity and so forth.

Referring to FIG. 5E, a user tap on touchpad 18 and/or one if its attendant buttons (here, again, left touchpad button 68) confirms the selection. As above, that tap can be conveyed by a notification from the touchpad subsystem 26b to the application 28a, which can again regenerate the user interface with further variation of the selected value. Alternatively (or in addition), as shown in FIG. 5F, confirmation of the selection can be signified by generation of a further user interface including further hotspots corresponding to the user's selection. In the drawing, that interface comprises three user-selectable hotspots 74, each with text and graphics identifying a patient of interest (e.g., a patient currently being treated and/or for whom medical treatment information is to be entered, recorded, output, or so forth). In practice, additional hotspots, such as "exit" and "back" buttons, may be included, as well.

Figures 6A, 6B, 6C:
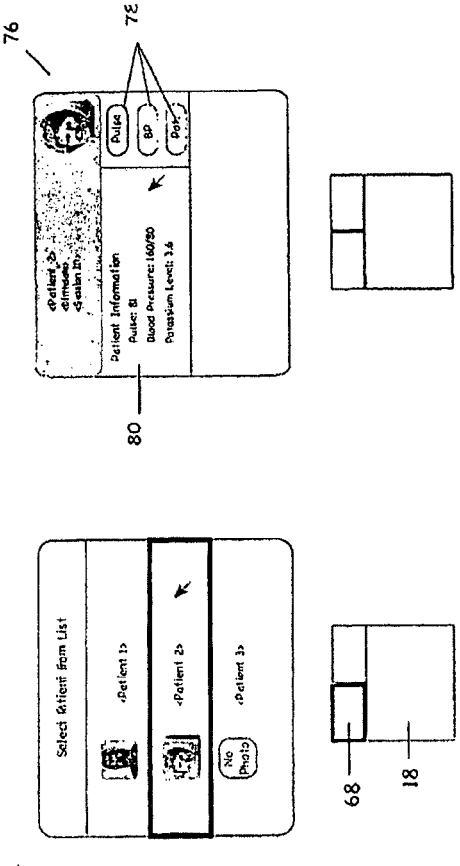

In a manner paralleling the actions described in connection with FIGS. 5A-5F, above, FIGS. 6A-6B depict selection of the hotspot corresponding to "Patient 2" via a two downward swipes on touchpad 18 (FIG. 6A) and confirmation of the hotspot via a tap (FIG. 6B). As an alternative to the use of two downward swipes in connection with the actions depicted in FIG. 6A, the application 28a of some embodiments can respond to a swipe of larger magnitude (as detected by touchpad subsystem 26b) to select a farther hotspot (i.e., one other than that nearest the cursor or currently activated hotspot in the direction of the swipe).

Figures 6D, 6E, 6F:
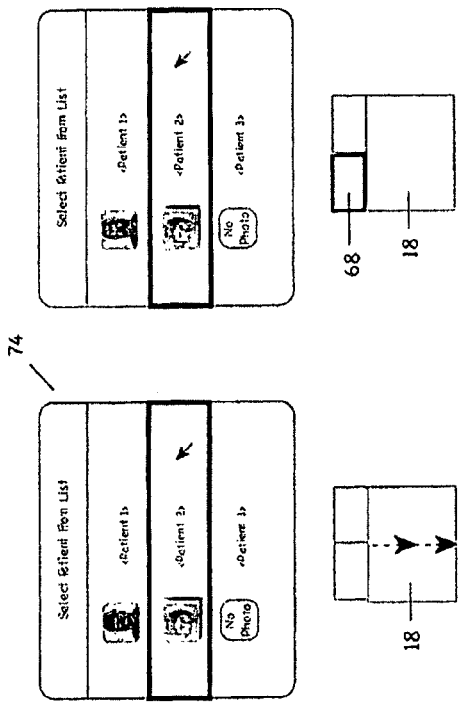

Continuing the example in the same vein as discussed above, FIG. 6C depicts a still further user interface including hotspot 80 generated by application 28a following confirmation of selection of the "Patient 2" hotspot in FIG. 6B. The interface includes, inter alia, three hotspots 78—here, user-selectable buttons for calling up the patient's pulse, blood pressure and/ or potassium level history and/or entering those values. As depicted in FIGS. 6D-6F, further swipes on the touchpad 18 can effect activation of those respective buttons: an upward right swipe for activation of the pulse button (FIG. 6D); a subsequent downward swipe for activation of the blood pressure button (FIG. 6E); and a further downward swipe for activation of the potassium levels button (FIG. 6F). As illustrated here and applicable throughout, in some embodiments, those swipes need not necessarily be confirmed, e.g., via a separate tap on the touchpad (or an associated touchpad button). More particularly, as shown in FIGS. 6D-6F, with activation of each of the respective hotspots/buttons 78, the application 28a displays additional corresponding hotspots 82—88, as shown.

Figure 7A:
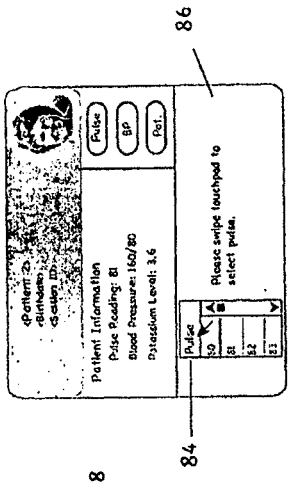
Figure 7B:
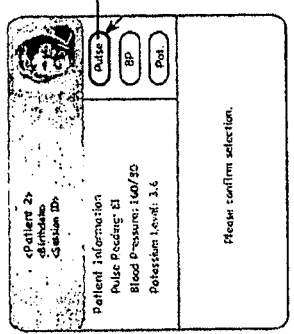
Figure 7C:
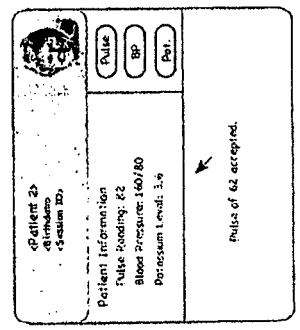
Figure 7D:
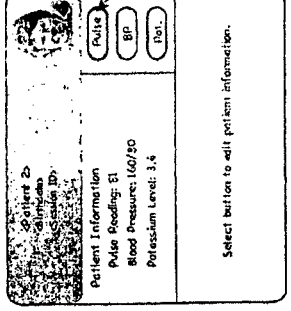
Figure 7E:
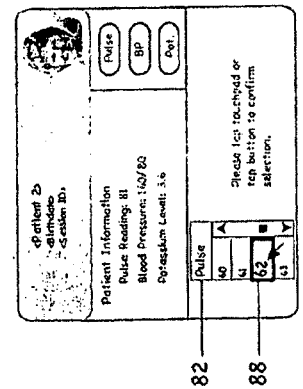

The hotspot activation depicted in FIG. 6D, is shown with further particularity in FIGS. 7A-7E, again, in a manner paralleling the actions described above. Thus, for example, FIGS. 7A-7C depicts selection of the pulse button from among hotspots 78. This mirrors the actions shown in FIG. 6D and described immediately above, albeit, here a separate tap on the touchpad or an associated touchpad button 68 is utilized to confirm the swipe (FIG. 7B) prior to display of the interface including the corresponding hotspot 82 (FIG. 7C). FIGS. 7D-7E illustrate use of touchpad swipes and taps in connection with menu hotspot 82 to select value 88 (here, a blood pressure value of "62") for input to application 28a. As above, that application can regenerate the interface, including new values for hotspot 82, with each user action. For example, following selection of the value 88, the application 28 generates confirmatory text identifying the selected value.

Figure 8A:
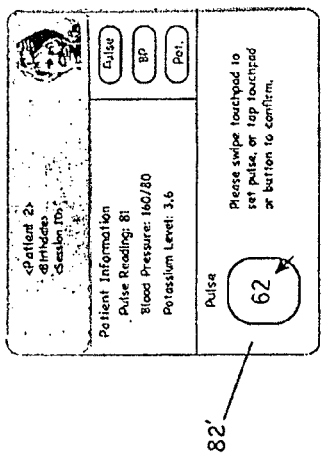
Figure 8A:
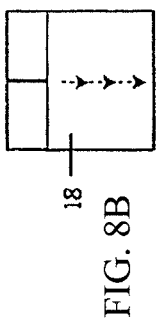
Figure 8B:
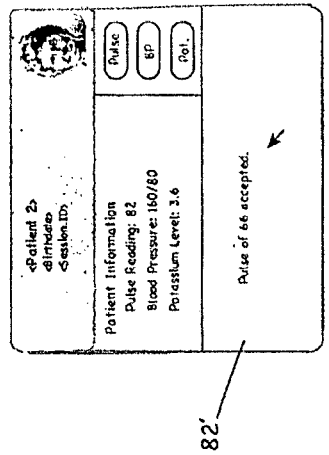
Figure 8B:
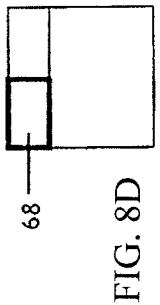
Figure 8C:
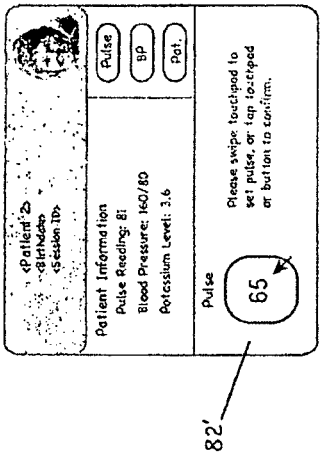
Figure 8C:
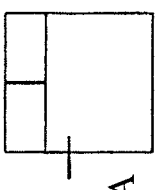
Figure 8D:
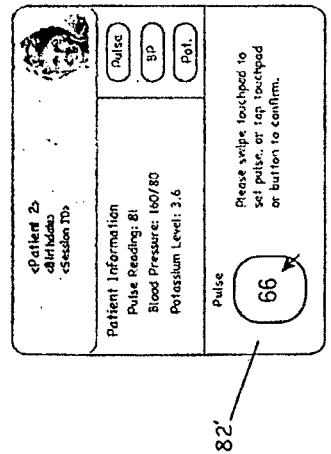
Figure 8D:
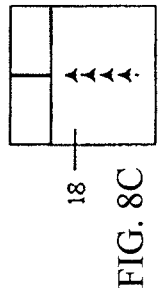

An alternate use of a hotspot for value selection and input is shown in FIGS. 8A-8D. This parallels the activity shown in FIGS. 7D-7E, albeit with a hotspot 82' that displays a user-adjustable value for pulse—absent, for example, a menu or "dial-wheel" metaphor. More particularly, following selection of the pulse button hotspot 78 as shown in FIG. 6D and discussed in connection therewith, application 28a regenerates the interface with hotspot 82' activated and a default value (here, 65) displayed. See, FIG. 8A. FIG. 8B depicts tentative adjustment of that value (to 62) via three downward swipes by the user on touchpad 18), and FIG. 8C depicts re-adjustment of that value (to 66) via four upward swipes. In FIG. 8D, the user confirms that value via a tap. As above, application 28a regenerates the interface, including new values for hotspot 82', with each user action. And, following confirmation (FIG. 8D), the application 28a generates confirmatory text identifying the selected value.

Figure 9:
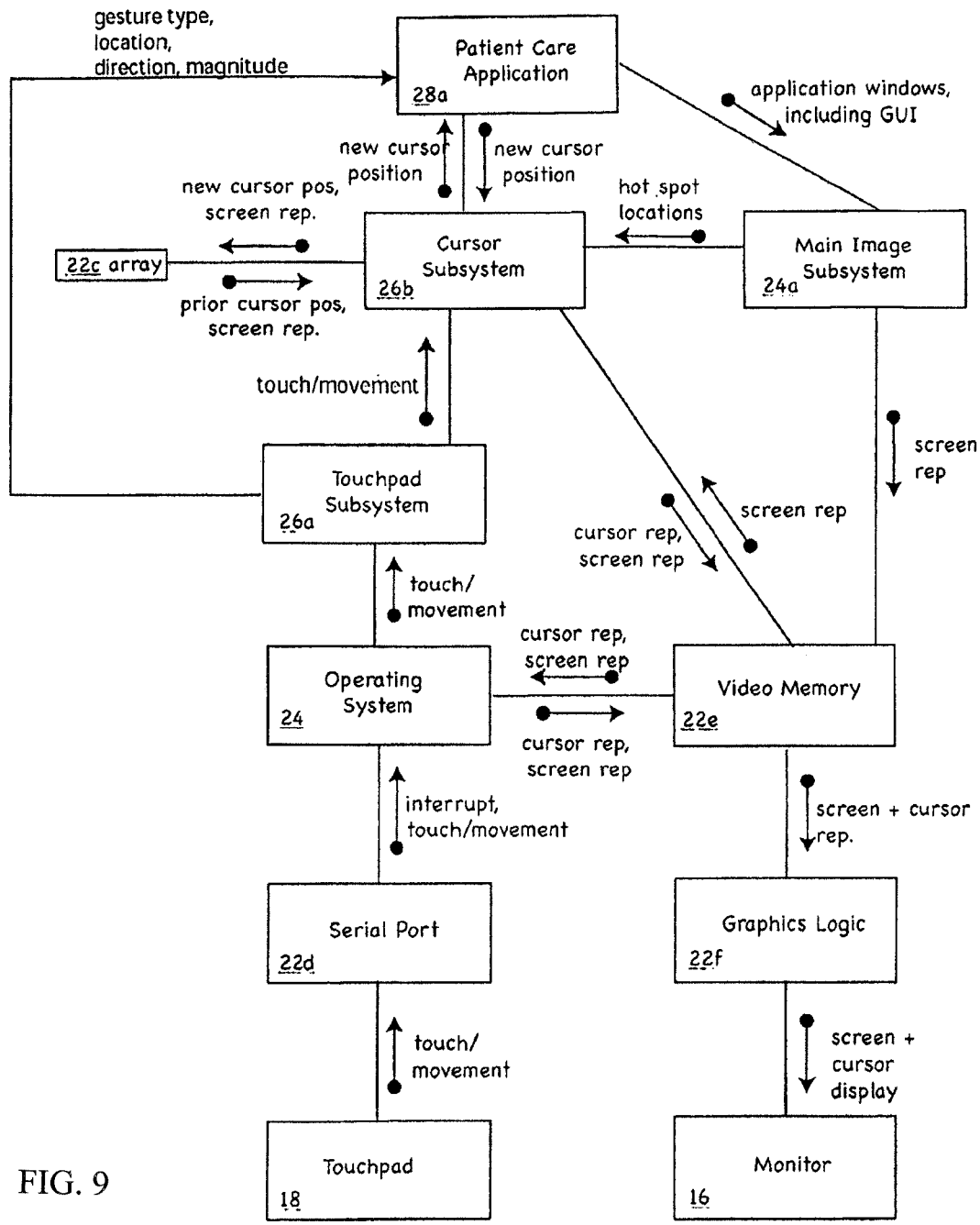
FIG. 9 is a data-flow diagram illustrating a flow of data and control signals in a system of the type shown in FIG. 1 for purposes of hotspot selection.

FIG. 9 is a data-flow diagram depicting, by way of non-limiting example, a manner in which the touchpad subsystem 26b identifies gestures and notifies application 28a and/or other element of the illustrated system, The data-flow of FIG. 9 parallels that of FIG. 3, discussed above, as adapted in view of the immediately preceding discussion of FIG. 5A-7E. Thus, for example, as shown in that drawing, a user of data entry station 10 effects activation of hotspots and selection of values within activated hotspots (collectively, "selection of hotspots") by touching and/or moving his/her finger on the touchpad 18 (or other device) in the conventional manner known in the art, as adapted in accord with the teachings hereof. The touchpad 18 responds by generating signals indicative of that touch/movement for input to serial port 22d, which in turn generates an interrupt for application to CPU 22a along with the touch/movement information—all in the conventional manner known in the art, as adapted in accord with the teachings hereof. Operating system 24 notifies touchpad subsystem 26b of the touchpad activity and makes that touch/movement information available to it. As above, this can be effected, by way of non-limiting example, by interrupt handling-code that comprises the and/or invokes the cursor subsystem 26a and that stores the touch/movement information to memory for use by it.

Upon notification of the touchpad activity, touchpad subsystem 26b determines what type of gesture it represents, e.g., touch, swipe, and so forth. It also retrieves from information supplied by the operating system 24 the location of the gesture, as well as its direction and magnitude. The touchpad subsystem supplies that information to application 28a, which determines, based on, the current position of the cursor and/or location of a currently activated hotspot, as well as on the gesture type, location, magnitude and/or direction what hotspot to activate or, in the event a hotspot is already activated, what user-selectable value associated with that hotspot to select—all in the manner as discussed, by way of non-limiting example, above. The application 28a regenerates an application window, including, text and graphics highlighting a newly activated hotspot or user-selectable value and passes it to the main image subsystem for generation of corresponding screen-representative signals, as discussed above.

The touchpad subsystem also supplies the touchpad touch/movement information, or a subset thereof, to cursor subsystem 26a, which assumes or calculates a tentative new cursor display position as discussed in connection with FIG. 3. The tentative position, however, may be overridden by values supplied by application 28a, based on its determination of the location of a newly activated hotspot and/or selection or a value associated therewith. The cursor subsystem 26a subsequently updates VRAM 22e as discussed above to effect repositioning of the cursor to that new location.

Described herein are systems, apparatus and methods meeting the objects set forth above, among others. It will be appreciated that the illustrated embodiments are merely examples of the invention and that other embodiments employing modifications of those illustrated and described here fall within the scope of the invention. Thus, graphics and/or text defining the user interface and attributed in the text above by the application 28a can be generated by the operating system 24 and/or middleware/software 26, instead or in addition. Likewise, response by the application 28a to notifications from the touchpad subsystem can be handled by functionality associated with the operating system 24 and/or the middleware/software 26, instead or in addition.

In view of the foregoing, what we claim is:

1. A patient treatment system for patient dialysis, comprising:
   one or more treatment apparatus comprising dialysis equipment;
   a digital data processor that is coupled for communications with the treatment apparatus;
   a user interface device that is coupled for communications with the digital data processor and with the one or more treatment apparatus;

the digital data processor performing one or more functions with respect to the user interface device and/or the treatment apparatus;

the digital data processor transmitting information to a remote computer system to facilitate execution of one or more of said functions, including generating text and graphics defining user interfaces for presentation on the user interface device to display information relating to, and to support operator interaction with, the medical treatment apparatus; and the remote computer system generating bit patterns and other representations of the text and graphics defining those user interfaces, and the digital data processor driving those bit patterns and other representations to the user interface device.

2. The patient treatment system of claim 1, wherein the digital data processor is coupled for communications with the treatment apparatus via a first communications link, and wherein the digital data processor is coupled for communications with the user interface device via a second communications link.

3. The patient treatment system of claim 2, wherein the user interface device is remote.

4. The patient treatment system of claim 2, wherein one or more of the first communications link and the second communications link are wireless.

5. The patient treatment system of claim 4, wherein one or more of the first communications link and the second communications link are Bluetooth communications links.

6. The patient treatment system of claim 2, wherein the second communications link is a wireless communication link.

7. The patient treatment system of claim 2, wherein the second communications link is a networked communications link.

8. The patient treatment system of claim 1, wherein the digital data processor is a stand-alone device.

9. The patient treatment system of claim 8, wherein the digital data processor is a stand-alone device with respect to one or more of the treatment apparatus and the user interface device.

10. The patient treatment system of claim 9, wherein the digital data processor is a stand-alone device with respect to both the treatment apparatus and the user input device.

11. The treatment system of claim 1, wherein the one or more functions facilitated include interfacing with the dialysis equipment.

12. The patient treatment system of claim 1, wherein the one or more functions facilitated include collecting and/or analyzing patient data.

13. The patient treatment system of claim 1, wherein the one or more functions facilitated include storing and/or transmitting data to databases and/or to the remote computer system.

14. The patient treatment system of claim 1, wherein the one or more functions facilitated include generating information for display on a monitor of the dialysis equipment.

15. The patient treatment system of claim 1, wherein the one or more functions facilitated include accepting the user input received at the user interface device.

16. The patient treatment system of claim 1, wherein one or more of the facilitate functions are implemented as web services.

17. The patient treatment system of claim 1, wherein the dialysis equipment is peritoneal dialysis equipment.

18. The patient treatment system of claim 1, wherein the dialysis equipment includes first and second dialysis apparatus.

19. The patient treatment system of claim 18, wherein the first and second dialysis apparatus are in communications coupling with the digital data processor wirelessly.

* * * * *